US00PP21050P2

(12) United States Plant Patent
Takeshita

(10) Patent No.: US PP21,050 P2
(45) Date of Patent: Jun. 1, 2010

(54) ***NEMESIA* PLANT NAMED 'KIRINE-44'**

(50) Latin Name: *Nemesia hybrida*
Varietal Denomination: Kirine-44

(75) Inventor: Daigaku Takeshita, Tochigi-ken (JP)

(73) Assignee: Kirin AgrioBio Co. Ltd., Tokyo (JP)

( * ) Notice: Subject to any disclaimer, the term of this patent is extended or adjusted under 35 U.S.C. 154(b) by 0 days.

(21) Appl. No.: 12/321,733

(22) Filed: Jan. 23, 2009

(51) Int. Cl.
*A01H 5/00* (2006.01)

(52) U.S. Cl. ..... Plt./458
(58) Field of Classification Search ..... Plt./263, Plt./458
See application file for complete search history.

*Primary Examiner*—Susan B McCormick Ewoldt
(74) *Attorney, Agent, or Firm*—C. A. Whealy

(57) ABSTRACT

A new and distinct cultivar of *Nemesia* plant named 'Kirine-44', characterized by its upright, outwardly spreading and uniformly mounded growth habit; freely branching and flowering plant habit; large creamy white-colored flowers that are fragrant; relatively tolerant to high temperatures; and good garden performance.

1 Drawing Sheet

Botanical designation: *Nemesia hybrida.*
Cultivar denomination: 'KIRINE-44'.

BACKGROUND OF THE INVENTION

The present invention relates to a new and distinct cultivar of *Nemesia* plant, botanically known as *Nemesia hybrida* and hereinafter referred to by the name 'Kirine-44'.

The new *Nemesia* plant is a product of a planned breeding program conducted by the Inventor in Tochigi, Japan. The objective of the breeding program is to create new *Nemesia* cultivars with good vigor and attractive flower coloration.

The new *Nemesia* plant originated from a cross-pollination made by the Inventor in February, 2007 in Tochigi, Japan of two unidentified selections of *Nemesia hybrida,* not patented. The new *Nemesia* was discovered and selected by the Inventor as a single flowering plant within the progeny of the stated cross-pollination in a controlled environment in Tochigi, Japan in October, 2007.

Asexual reproduction of the new *Nemesia* plant by terminal cuttings in a controlled environment in Tochigi, Japan since November, 2007, has shown that the unique features of this new *Nemesia* plant are stable and reproduced true to type in successive generations.

SUMMARY OF THE INVENTION

Plants of the new *Nemesia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kirine-44'. These characteristics in combination distinguish 'Kirine-44' as a new and distinct cultivar of *Nemesia:*

1. Upright, outwardly spreading and uniformly mounded growth habit.
2. Freely branching and flowering plant habit.
3. Large creamy white-colored flowers that are fragrant.
4. Relatively tolerant to high temperatures.
5. Good garden performance.

Plants of the new *Nemesia* can be compared to plants of the parent selections. Plants of the new *Nemesia* are more vigorous and have larger flowers than plants of the female parent selection and smaller flowers than plants of the male parent selection.

Plants of the new *Nemesia* can be compared to plants of the *Nemesia* 'Kirine-4', disclosed in U.S. Plant Pat. No. 18,271. In side-by-side comparisons conducted in De Lier, The Netherlands, plants of the new *Nemesia* differed primarily from plants of 'Kirine-4' in the following characteristics:

1. Plants of the new *Nemesia* were more mounding and denser than plants of 'Kirine-4'.
2. Plants of the new *Nemesia* and 'Kirine-4' differed in flower color as plants of 'Kirine-4' had more yellow-colored flowers.

Plants of the new *Nemesia* can also be compared to plants of the *Nemesia* 'Intraiwhi', disclosed in U.S. Plant Pat. No. 17,502. In side-by-side comparisons conducted in De Lier, The Netherlands, plants of the new *Nemesia* differed primarily from plants of 'Intraiwhi' in the following characteristics:

1. Plants of the new *Nemesia* were stronger and sturdier than plants of 'Intraiwhi'.
2. Plants of the new *Nemesia* had larger flowers than plants of 'Intraiwhi'.

BRIEF DESCRIPTION OF THE PHOTOGRAPHS

The accompanying colored photographs illustrate the overall appearance of the new *Nemesia*, showing the colors as true as it is reasonably possible to obtain in colored reproductions of this type. Colors in the photographs may differ slightly from the color values cited in the detailed botanical description which accurately describe the colors of the new *Nemesia.*

The photograph on the first sheet comprises a side perspective view of a typical flowering plant of 'Kirine-44' grown in a container.

DETAILED BOTANICAL DESCRIPTION

Plants used for the aforementioned photographs and following description were grown under conditions which closely approximate commercial production conditions during the summer and autumn in a glass-covered greenhouse in De Lier, The Netherlands for twelve weeks in containers. During the production of the plants, day temperatures ranged from 17° C. to 30° C. and night temperatures ranged from 16° C. to 18° C. In the following description, color references are made to The Royal Horticultural Society Colour Chart, 2001 Edition, except where general terms of ordinary dictionary significance are used.

Botanical classification: *Nemesia hybrida* 'Kirine-44'.

Parentage:

*Female, or seed, parent.*—Unidentified selection of *Nemesia hybrida,* not patented.

*Male, or pollen, parent.*—Unidentified selection of *Nemesia hybrida,* not patented.

Propagation:

*Type.*—By terminal cuttings.

*Time to initiate roots, summer.*—About four to seven days at 18° C. to 20° C.

*Time to initiate roots, winter.*—About seven to ten days at 18° C. to 20° C.

*Time to produce a rooted young plant, summer.*—About two weeks at 16° C. to 20° C.

*Time to produce a rooted young plant, winter.*—About three weeks at 16° C. to 20° C.

*Root description.*—Medium in thickness, fibrous; creamy white in color.

*Rooting habit.*—Freely branching; moderately dense.

Plant description:

*Plant and growth habit.*—Upright, outwardly spreading and uniformly mounded growth habit. Freely branching habit with lateral branches potentially forming at every node; pinching enhances lateral branch development. Moderately vigorous growth habit.

*Plant height.*—About 13 cm to 15 cm.

*Plant diameter.*—About 27 cm to 30 cm.

Lateral branch description:

*Length.*—About 8 cm to 9 cm.

*Diameter.*—About 2 mm.

*Internode length.*—About 1.5 cm to 3 cm.

*Strength.*—Strong.

*Aspect.*—Upright to outwardly spreading.

*Texture.*—Smooth, glabrous.

*Color.*—Close to 146A.

Foliage description:

*Arrangement.*—Opposite, simple; sessile.

*Length.*—About 4.5 cm.

*Width.*—About 1.8 cm to 2 cm.

*Shape.*—Lanceolate.

*Apex.*—Acute.

*Base.*—Cuneate.

*Margin.*—Serrate.

*Texture, upper and lower surfaces.*—Smooth, glabrous.

*Venation pattern.*—Pinnate; arcuate.

*Color.*—Developing leaves, upper surface: Close to 144A. Developing leaves, lower surface: Close to 146B. Fully expanded leaves, upper and lower surfaces: Close to 137B; venation, close to 137B.

Flower description:

*Flower arrangement and flowering habit.*—Zygomorphic bilabiate flowers arranged on terminal racemes; flowering acropetally towards the apex; flowers face upright and outwardly; freely flowering habit with about 20 to 24 flowers developing per raceme.

*Flower longevity.*—Flowers last about five to seven days on the plant; flowers not persistent.

*Fragrance.*—Moderately fragrant; floral, pleasant.

*Natural flowering season.*—In The Netherlands, plants flower from spring to fall; flowering continuous during this period; plants begin flowering about five to seven weeks after planting.

*Inflorescence height.*—About 3 cm to 4 cm.

*Inflorescence diameter.*—About 5 cm.

*Flower height.*—About 2.5 cm to 3 cm.

*Flower diameter.*—About 2.5 cm to 2.8 cm.

*Flower depth.*—About 1 cm to 1.8 cm.

*Flower buds.*—Shape: Ovoid. Length: About 1.4 cm. Diameter: About 5 mm to 7 mm. Color: Close to 155B.

*Petals.*—Arrangement: Five petals; four upper petals are fused at base to form an upright lobed and arched banner lip; lower petal modified into a larger lip with convex oval protuberance with serves as a pollinator nectar guide and landing platform. Shape: Oval to rounded. Apex: Rounded. Margin: Entire; lower lip, slightly sinnuate. Length: Upper petals: About 2 cm. Lower petal: About 2 cm. Width: Upper petals: About 2.5 cm. Lower petal: About 2.5 cm. Texture, upper and lower surfaces: Smooth, glabrous. Color, upper and lower petals: When opening, upper and lower surfaces: Close to N155C. Fully opened, upper surface: Upper petals, close to N155C, nectar guides at the base, close to 93A; lower petal, close to N155C, protuberance, close to 25A. Fully opened, lower surface: Close to N155C.

*Sepals.*—Arrangement: Calyx star-shaped with five sepals fused at the base. Shape: Lanceolate. Apex: Acute. Margin: Entire. Length: About 6 mm to 7 mm. Width: About 2 mm. Texture, upper and lower surfaces: Pubescent. Color, upper surface: Close to 144A. Color, lower surface: Close to 146B.

*Peduncles.*—Length: About 3 cm. Diameter: About 2 mm. Angle: Erect to about 45° from vertical. Strength: Strong. Texture: Scattered pubescence. Color: Close to 146A.

*Pedicels.*—Length: About 1 cm. Diameter: About 1 mm. Angle: About 45° from peduncle axis. Strength: Moderately strong. Texture: Pubescent. Color: Close to 146B.

*Reproductive organs.*—Stamens: Quantity/arrangement: Four per flower. Filament length: About 1.5 mm to 3.5 mm. Filament color: Close to 155D. Anther shape: Oval. Anther length: Less than 1 mm. Anther color: Close to 17A. Pollen amount: Scarce. Pollen color: Close to 162A. Pistils: Quantity: One per flower. Pistil length: About 2 mm. Style length: About 1 mm. Style color: Close to 145C. Stigma shape: Rounded. Stigma color: Close to 145C. Ovary color: Close to 146B. Seed/fruit: Seed and fruit development have not been observed on plants of the new *Nemesia.*

Pathogen/pest resistance: Plants of the new *Nemesia* have not been observed to be resistant to pests and pathogens common to *Nemesia.*

Garden performance: Plants of the new *Nemesia* have been observed to tolerate wind and rain and have good garden performance.

Temperature tolerance: Plants of the new *Nemesia* have been observed to tolerate temperatures from about 0° C. to about 28° C.

It is claimed:

1. A new and distinct *Nemesia* plant named 'Kirine-44' as illustrated and described.

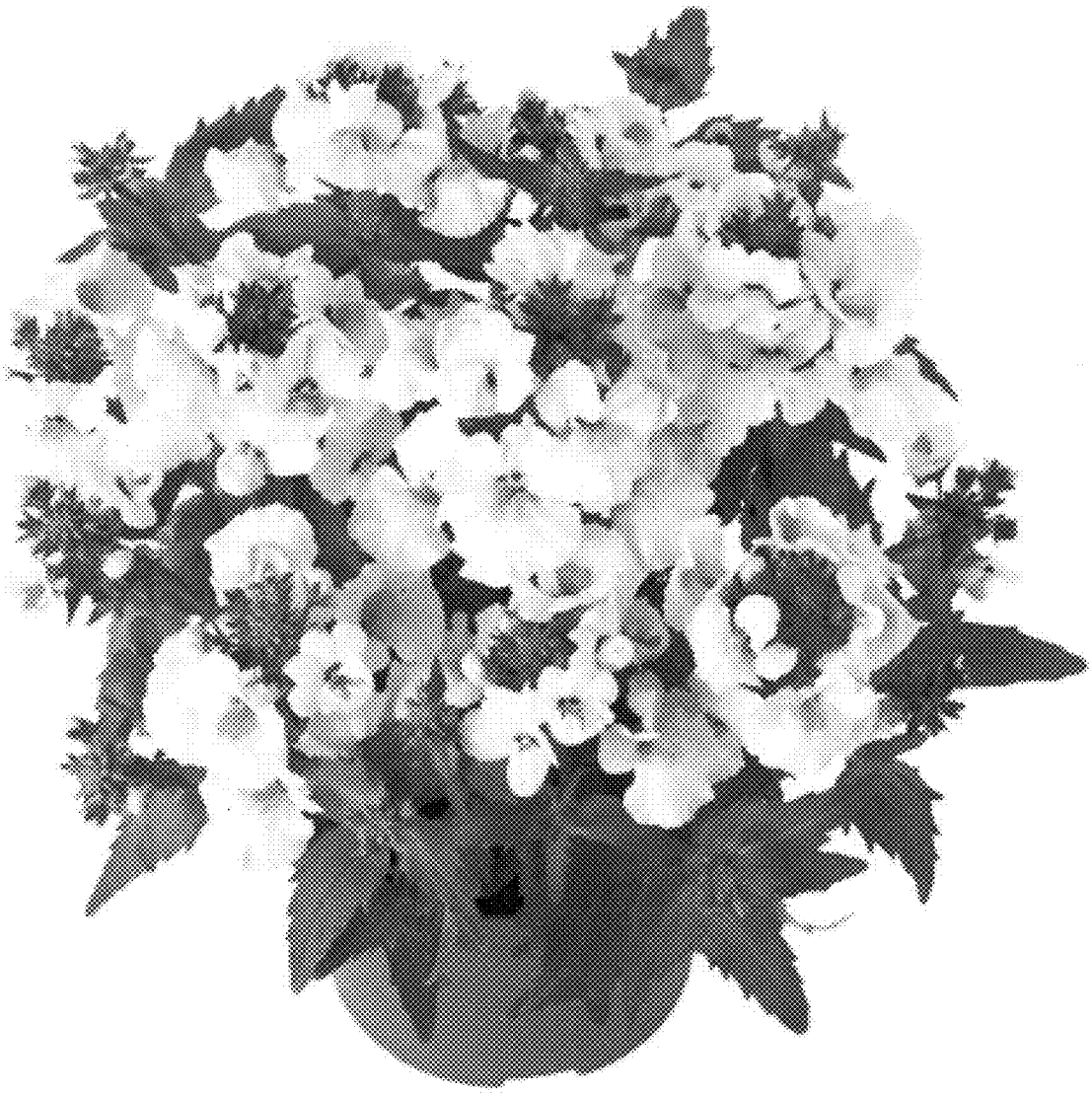

* * * * *